United States Patent
Hall et al.

(10) Patent No.: US 10,241,122 B2
(45) Date of Patent: Mar. 26, 2019

(54) METHOD OF MEASURING ARTIFICIAL SWEETENERS IN BODILY WASTE TO IDENTIFY AND QUANTIFY DRUG CONSUMPTION

(71) Applicants: David R. Hall, Provo, UT (US); Steven Butala, Provo, UT (US); Dan Allen, Springville, UT (US); Daniel Hendricks, Provo, UT (US); Andrew Nguyen, Provo, UT (US); Conrad Rosenbrock, Provo, UT (US); Terrece Pearman, Draper, UT (US)

(72) Inventors: David R. Hall, Provo, UT (US); Steven Butala, Provo, UT (US); Dan Allen, Springville, UT (US); Daniel Hendricks, Provo, UT (US); Andrew Nguyen, Provo, UT (US); Conrad Rosenbrock, Provo, UT (US); Terrece Pearman, Draper, UT (US)

(*) Notice: Subject to any disclaimer, the term of this patent is extended or adjusted under 35 U.S.C. 154(b) by 252 days.

(21) Appl. No.: 15/472,989

(22) Filed: Mar. 29, 2017

(65) Prior Publication Data

US 2018/0284144 A1    Oct. 4, 2018

(51) Int. Cl.

| G01N 33/58 | (2006.01) |
|---|---|
| G01N 33/94 | (2006.01) |
| G01N 33/493 | (2006.01) |
| A61B 5/00 | (2006.01) |
| G01N 21/64 | (2006.01) |
| A61B 10/00 | (2006.01) |
| A61B 5/145 | (2006.01) |

(Continued)

(52) U.S. Cl.
CPC ........... *G01N 33/94* (2013.01); *G01N 33/493* (2013.01); *G01N 33/58* (2013.01); *A61B 5/0075* (2013.01); *A61B 5/1455* (2013.01); *A61B 5/14507* (2013.01); *A61B 5/207* (2013.01); *A61B 5/7271* (2013.01); *A61B 10/0038* (2013.01); *A61B 2010/0006* (2013.01); *G01N 2021/6417* (2013.01); *G01N 2021/6439* (2013.01); *G01N 2458/00* (2013.01); *G01N 2800/52* (2013.01)

(58) Field of Classification Search
CPC ........ A61B 10/0038; A61B 2010/0006; A61B 5/0075; A61B 5/14507; A61B 5/1455; A61B 5/207; A61B 5/7271; G01N 33/493; G01N 33/94; G01N 2021/6417; G01N 2021/6439; G01N 2458/00; G01N 33/58

See application file for complete search history.

(56) References Cited

U.S. PATENT DOCUMENTS

| 9,671,343 B1 * | 6/2017 | Hall | .................. G01N 21/6428 |
| 2016/0000378 A1 * | 1/2016 | Hall | ..................... A61B 5/0075 |
| | | | 702/19 |

* cited by examiner

*Primary Examiner* — Jennifer Wecker (57) ABSTRACT

We disclose a drug tracking system and method of use which may be used to screen a subject's bodily waste in order to assess whether the subject has consumed a drug. The system includes a drug composition which is tagged with at least one artificial sweetener that may be detected in the subject's bodily waste. The subject may consume the tagged drug and a user may obtain a sample of the subject's bodily waste. The bodily waste sample may be analyzed to detect the artificial sweetener or its metabolite. In some embodiments, the result of the analysis of bodily waste may be entered into a database, compared to standards that comprises analyses of a plurality of drug tags, and the identity of the drug tag, and consequently the drug composition, determined.

20 Claims, 7 Drawing Sheets

(51) Int. Cl.
*A61B 5/1455* (2006.01)
*A61B 5/20* (2006.01)

| Artificial Sweetener | Chemical Structure |
|---|---|
| Aspartame | |
| Acesulfame K | |
| Saccharine | |
| Sucralose | |
| Neotame | |
| Sodium Cyclamate | |
| Calcium Cyclamate | |
| Cyclamic Acid | |
| Polyethylene Glycol | |

FIG. 1

| Steviol Glycoside | Chemical Structure | Steviol Glycoside | Chemical Structure |
|---|---|---|---|
| Stevioside | | Rebaudioside D | |
| Rebaudioside A | | Rebaudioside E | |
| Rebaudioside C | | Dulcoside A | |
| Rebaudioside B | | Rubusoside | |

FIG. 2

| Sugar Alcohol | Chemical Structure | Sugar Alcohol | Chemical Structure |
|---|---|---|---|
| Arabitol | | Maltitol | |
| Erythritol | | Maltotetraitol | |
| Fucitol | | Maltotriitol | |
| Galactitol | | Mannitol | |
| Glycerol | | Ribitol | |
| Iditol | | Sorbitol | |
| Inositol | | Threitol | |
| Isomalt | | Volemitol | |
| lactitol | | Xylitol | |

FIG. 3

| Artificial Sweetener | Metabolite |
|---|---|
| Neotame | N-[N-(3,3-dimethylbutyl)-L-alpha-aspartyl]-L-phenylalanine |
| Na Cyclamate | Cyclohexylamine |
| Steviol | Steviol glucuronide |

METHOD OF MEASURING ARTIFICIAL SWEETENERS IN BODILY WASTE TO IDENTIFY AND QUANTIFY DRUG CONSUMPTION

BACKGROUND

Field of the Invention

This disclosure relates to methods of tracking and identifying pharmaceuticals after consumption, particularly by screening bodily waste for drug markers.

Background of the Invention

The consumption of drugs is largely untracked. This is particularly problematic when dealing with issues that include drug addiction, drug compliance, and dosing control and adjustment. For example, it is difficult to assess whether an individual who is being treated with opioid replacement therapy (ORT) while being weaned off opioid use is taking the prescribed longer acting but less euphoric opioid or has relapsed into using the drug of abuse. It is also difficult to interpret clinical studies when drug compliance of study subjects is inconsistent.

Tracking of drugs in the human waste stream is desirable. Drug tracking molecules with a known safety record are also desirable. A drug tracking molecule that is commonly added to food and which has been studied with regard to its pharmacokinetics, stability, metabolism, and adverse effects would be an attractive candidate. In addition, a drug tracking molecule that may be detected in the human waste stream using noninvasive and well-established analytical methods would be useful.

Artificial sweeteners have been used for decades in place of sugars. These molecules provide the sweet taste sensation but are not significantly absorbed. May are not metabolized or are metabolized to products that are not significantly absorbed. Therefore, when these artificial sweeteners are consumed, most of the artificial sweeteners or their metabolites are excreted in urine and feces. Accordingly, artificial sweeteners have very few calories while providing the sweet taste of a larger volume of sugar. Consequently, they are used in foods in place of sugar for purposes of weight loss and for people with metabolic diseases including diabetes. At least because of these uses and properties, the artificial sweeteners have been thoroughly studied. For at least these reasons, artificial sweeteners represent attractive candidates for tagging drugs to identify and/or quantify drug consumption.

BRIEF SUMMARY OF THE INVENTION

We disclose a drug tracking system which includes a drug tracking tag that may be identified in bodily waste. The drug tracking tag may be one or more artificial sweeteners. The artificial sweeteners may be excreted in bodily waste either unchanged or in the form of detectable metabolites.

A user may obtain a sample of the subject's bodily waste and analyze the sample to detect artificial sweeteners or metabolites thereof. The analysis may be accomplished using known analytical techniques. In some embodiments, the analysis may be accomplished using a medical toilet. The medical toilet may include spectroscopy equipment, equipment to perform various forms of chromatography, and other analytical techniques which may be used to analyze bodily waste.

In some embodiments, the user may enter the results of the analysis of the subject's bodily waste into a database. The database may store standards which comprise analytical results acquired by detecting the various drug tags that are in use. The database may be associated with computer readable medium which may compare the analysis of the user's bodily waste to the various standards and find a match. The artificial sweeteners used to create the standard are identified and then the drug which is tagged with that artificial sweetener is identified. The disclosed methods may be used for a variety of purposes including confirming drug compliance, screening for drug interactions, and assessing whether a subject has consumed a drug to which the subject has an allergy.

DETAILED DESCRIPTION OF THE INVENTION

Definitions

Drug, as used herein, means any pharmacologically active agent or mixture of agents.

Drug consumption, as used herein, means taking a drug into the body through any method of administration.

Bodily waste, as used herein, means urine, feces, or a combination of urine and feces.

Subject, as used herein, means a patient, a participant in a medical study, or any individual who has consumed a drug composition which includes a drug tag as described herein.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a drug tracking system which includes a method of tracking drug consumption by a subject. One advantage of the disclosed drug tracking system is that the disclosed method does not require a technique to measure the drug or its metabolite directly. Rather the disclosed method detects artificial sweeteners which may be used as a tag for the drug. A different artificial sweetener may be used to tag each of a plurality of drugs. Alternatively, multiple artificial sweetener may be used to tag a drug. In some embodiments, multiple artificial sweeteners which are present in defined ratios may be used to tag a drug. The artificial sweetener may be applied to the drug by spraying or painting the artificial sweetener on the drug, mixing the artificial sweetener with the drug, or other methods known in the art. Each tagged drug may be associated with a different artificial sweetener. Each artificial sweetener may be detected using a the same or different analytical techniques. While the drug may separate from the artificial sweetener after consumption, the excreted artificial sweetener in bodily waste is still indicative of consumption of the drug.

Another advantage of the disclosed drug tracking system is that artificial sweetener or its metabolite may be detected in bodily waste, including urine, using well-established analytical techniques. In some embodiments, the analytical techniques may be conducted by analytical equipment that is housed within a medical toilet. In this embodiment, the artificial sweetener or its metabolite may be detected in a convenient and unobtrusive matter. The subject simply urinates or defecates normally into the bowl of the medical toilet and the analytical equipment within the medical toilet detects the artificial sweetener or its metabolite.

In an example of a method of using the disclosed drug tracking system, a subject may consume one or more drugs which have each been tagged with one or more artificial sweeteners. The artificial sweetener, combination of artificial sweeteners, or a defined ratio of multiple artificial sweeteners may be unique to each drug. The user may obtain a sample of the subject's biological waste. The user may then conduct an analysis of the user's biological waste to identify the presence of the artificial sweetener, multiple artificial sweeteners, or reaction products thereof.

In some embodiments, the bodily waste may be urine. Urine from a may be more or less dilute depending on the hydration status of the subject. Consequently, it may be useful to normalize the signal obtained from measuring the artificial sweetener and or its metabolites to a measurement of another characteristic of the urine. For example, the user may conduct a measurement of a urine metabolite or measure the urine specific gravity. The user may normalize the measurements of one or more artificial sweeteners and/or their metabolites to the measurement of the urine metabolite or urine specific gravity. This may provide a more quantitative measurement of the one or more artificial sweeteners and/or their metabolites. Accordingly, some embodiments of the disclosure may include the step of calculating a normalized measurement of the one or more artificial sweetener, one or more reaction products of artificial sweeteners, or combinations thereof in the bodily waste sample.

In addition, a user may wish to include a control measurement which may act as an assessment of renal clearance or excretion in the feces. Ideally, a biomarker which is completely or nearly completely excreted in the biological waste may be used as the control. In one embodiment, para-aminobenzoic acid (PABA) may be included in the drug as a biomarker along with the one or more artificial sweeteners. PABA is nearly completely excreted in urine (Bingham et al., British Journal of Nutrition (1995), 73, 531-550). Consequently, the subject's ability to excrete the biomarker in urine may be compared to the measurements of the sweeteners and/or their metabolites to confirm reliability. In some embodiments, the analysis of the subject's bodily waste may be expressed as a ratio of the measurement of the artificial sweetener(s) or metabolites thereof in the bodily waste sample and the measurement of the biomarker in the bodily waste. Alternatively the analysis of the subject's bodily waste may be normalized to a characteristic of the urine and that calculated number may then be expressed in terms of the measurement of the biomarker in the bodily waste.

In some embodiments, a bodily waste sample may be collected from the same subject multiple times over a period of time. The one or more artificial sweetener and/or metabolites thereof may be detected in each bodily waste sample. A user may perform a trending analysis with the data set to determine the subject's drug consumption over time. This may be used, for example, to compare drug use with biological events, drug efficacy, and drug potency.

Examples of artificial sweeteners which may be used as drug tracking molecules according to the disclosure, alone or in combination, include, but are not limited to acesulfame K, saccharine, sucralose, steviol glycoside, neotame, aspartame, cyclamic acid, calcium cyclamate, sodium cyclamate, polyethylene glycol, and sugar alcohols. Some examples of sugar alcohols which may be used as drug tracking molecules according the disclosure include, but are not limited to, arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol, and xylitol.

In some embodiment, the artificial sweetener may be excreted in the bodily waste unchanged from its original form. In some embodiments, approximately 80% to approximately 100% of the artificial sweetener may be excreted unchanged from its original form. In other embodiments, at least some of the artificial sweetener may be metabolized in the subject's body to a reaction product which may be detected in the subject's bodily waste. Examples of reaction products of artificial sweetener which may be detected in a subject's bodily waste according to the disclosure include, but are not limited to, cyclohexylamine, steviol glucuronide, and N—[N-(3,3-dimethylbutyl)-L-alpha-aspartyl]-L-phenylalanine.

The artificial sweeteners and their reaction products may be detected in bodily waste samples using a variety of analytical techniques. These techniques include, but are not limited to, gas chromatography-mass spectrometry, liquid chromatography, capillary zone electrophoresis with UV absorbance, high performance liquid chromatography with UV absorbance, reverse-phase chromatography, fluorescence spectroscopy, high performance thin layer chromatography, infrared spectroscopy, UV spectroscopy, near IR spectroscopy, nuclear magnetic resonance, ion mobility spectrometry, liquid chromatography-ion mobility spectroscopy. liquid chromatography-electrochemical detection, liquid chromatography-UV spectroscopy with a normal UV photodetector, thin layer chromatography, liquid chromatography, and Raman spectroscopy.

While some artificial sweeteners are amenable to detection in the form in which they are excreted in bodily waste, others may be more readily detected by reacting the artificial sweetener in the bodily waste sample to form a derivative of the artificial sweetener. Then, an analytical method may be used to detect the derivative. Examples of derivatives which may be formed from artificial sweeteners excreted in bodily waste include, but are not limited to, N—[N-(3,3-dimethylbutyl)-L-alpha-aspartyl]-L-phenylalanine which may be created from neotame, cyclohexylamine, which may be created from sodium cyclamate, and steviol glucuronide, which may be created from steviol.

Some embodiments of the disclosed drug tracking system include the use of a database. The database may store multiple analytical results which were created by analyzing multiple drug tags and which are used as standards. These drug tags may include one or more artificial sweeteners as disclosed herein, and/or their reaction products. The standards may also include analyses of multiple artificial sweeteners which were provided in a defined ratio. The ratio may be part of the drug tag. Accordingly, the database may include analytical results of multiple drug tags which may be used to compare with the analysis of the subject's bodily waste sample.

Upon obtaining the subject's bodily waste sample and conducting an analysis of the bodily waste sample, the user may enter the results of the analysis into the database. The user may use computer readable medium to compare the result of the analysis of the bodily waste to the stored standards. The computer readable medium may identify at least one standard which matches, or at least approximates, the analysis of the user's bodily waste. If the subject has consumed more than one drug comprising a drug tag, multiple standards may match parts of the analysis of the bodily waste sample. The user may then identify the one or more artificial sweetener which was used to produce the standard. The artificial sweeteners which were analyzed to create the standards may also be stored in the database.

The user may then identify the drug associated with the one or more artificial sweeteners used to create the standard which matches the analysis of the subject's bodily waste. In other words, the user may identify which drug was tagged with the one or more artificial sweeteners which were analyzed to create the standard that matched the analysis of the subject's bodily waste sample. The user may thereby, identify which drug the subject has consumed. The drug associated with each drug tag may also be store in the database.

In some embodiments, the identification of the one or more drugs the subject has consumed may be used to confirm that the user has been compliant in taking prescription medications that were prescribed to the user. In some embodiments, the database may store or have access to information about the subject's prescribed medication. The computer readable medium associated with the database may perform the comparison of the drug identified according to the disclosed drug tracking system and those prescribed to the subject.

In addition, the disclosed drug tracking system may be used to compare the drugs identified as being consumed by the subject using the disclosed drug tracking system with drugs to which the subject has known allergies. In some embodiments, the database may store or have access to information about the subject's drug allergies. The computer readable medium associated with the database may perform the comparison of the drug identified according to the disclosed drug tracking system and the drugs to which the subject has known allergies.

Similarly, the disclosed drug tracking system may be used to compare the drugs identified as being consumed by the subject using the disclosed drug tracking system with drugs which are known to interact poorly and result in adverse events. In some embodiments, the database may store or have access to a list of known drug interactions. The computer readable medium associated with the database may perform the comparison of the drugs identified according to the disclosed drug tracking system and the drugs known to result in adverse drug interactions.

Referring now to the drawings, FIGS. 1-4 include tables which provide the names and chemical structures of artificial sweeteners which may be used as drug tags according to the disclosure as well as their metabolites which may be measured in bodily waste.

Figure 1:
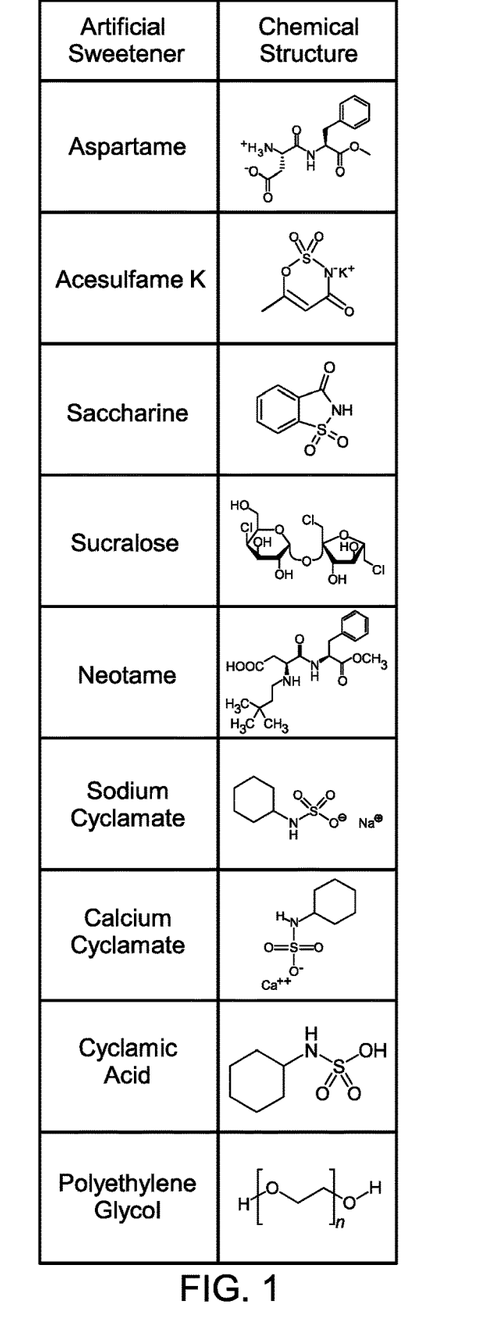
FIG. 1 is a table showing the names and chemical structures of examples of artificial sweeteners which may be used as drug tags according to the disclosure.

FIG. 1 is a table showing several examples of artificial sweeteners and their chemical structures. These artificial sweeteners may be used as drug tags, alone or in combination, according to the disclosure. These include artificial sweeteners that are detectable in bodily waste by measuring the unchanged sweetener or a reaction product thereof. Most are minimally changed prior to excretion and all are at least partially cleared by the renal system.

Figure 2:
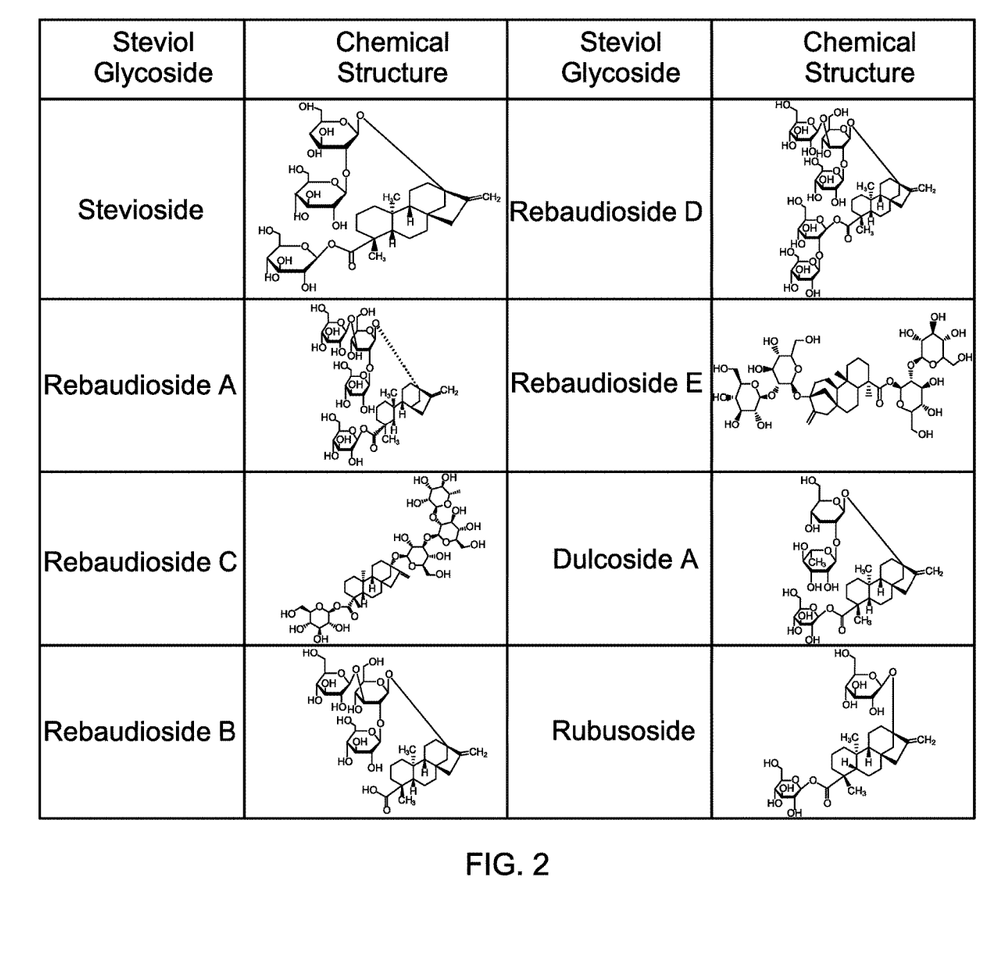
FIG. 2 is a table showing the names and the chemical structures of examples of steviol glycosides which may be measured in bodily waste according to the disclosure.

FIG. 2 is a table showing several steviol glycosides and their chemical structures. These are glycosylation products of steviol and all but rubusoside have been isolated from the plant *Stevia rebaudiana*. Rubusoside is a steviol glycoside found in the plant *Rubus chingii*. Steviol glycosides may be used alone are with other artificial sweeteners as drug tags according to the disclosure. Steviol glycosides are excreted in the urine at least in part as steviol glucuronide (Geuns et al., J. Agric. Food Chem. (2006), 54, 2794-2798) which may be detected in urine according to the disclosure.

Figure 3:
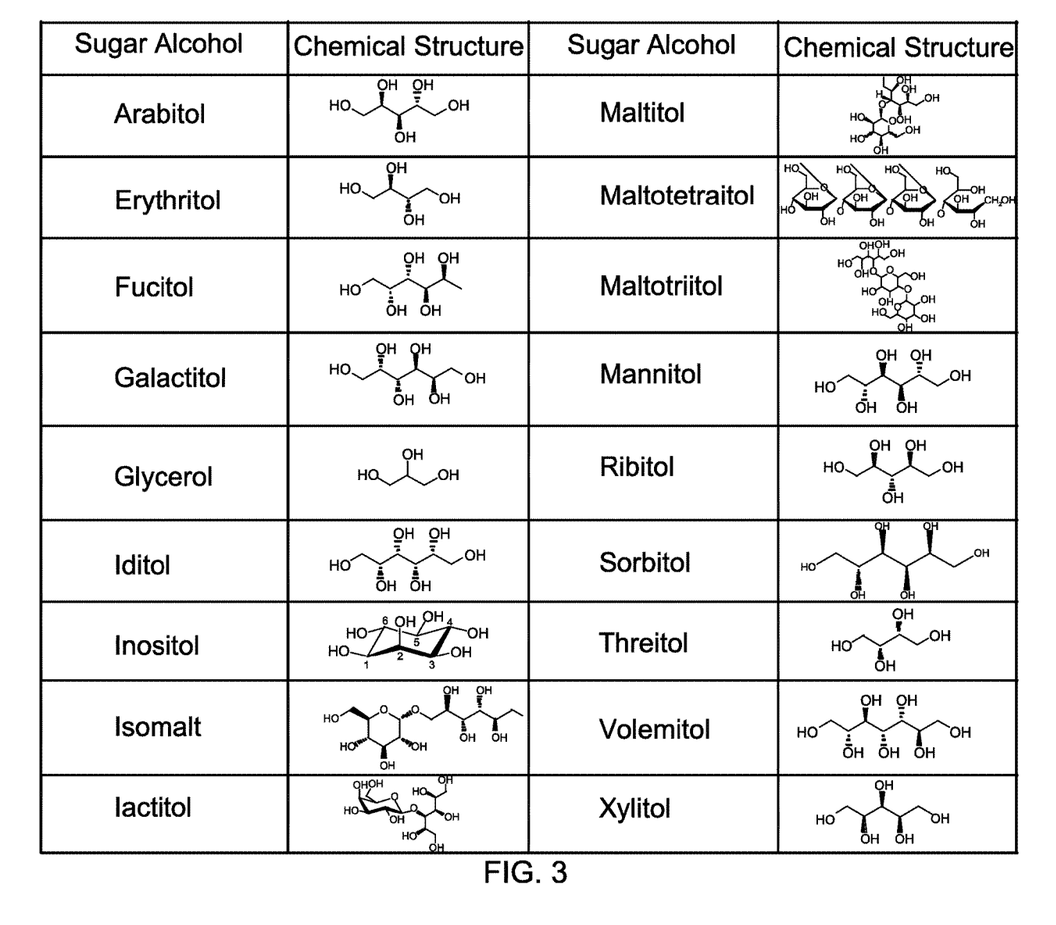
FIG. 3 is a table showing the names and the chemical structures of examples of sugar alcohols which may be used as drug tags according to the disclosure.

FIG. 3 is a table showing several sugar alcohols and their chemical structures. These sugar alcohols are used as artificial sweeteners and may be used as drug tags, alone or in combination with other artificial sweeteners, according to the disclosure.

Figure 4:
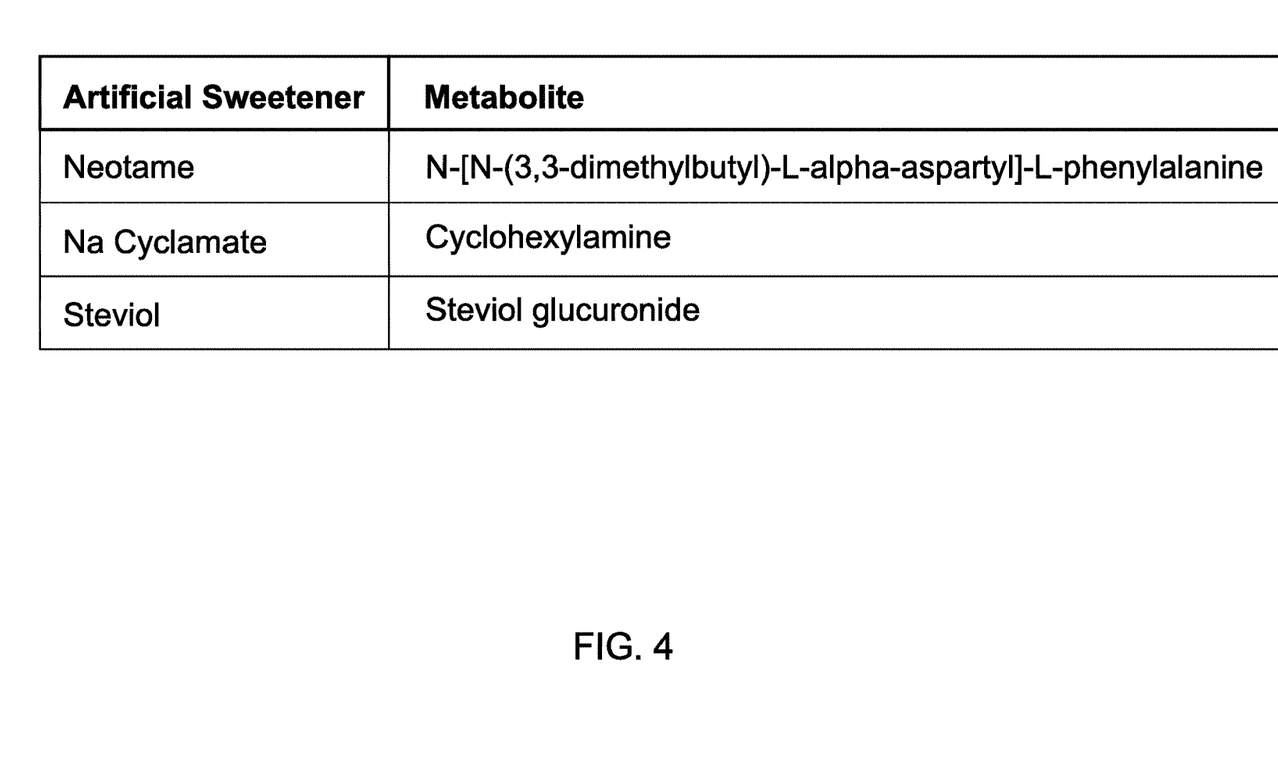
FIG. 4 shows the names of examples of artificial sweeteners which may be used as drug tags according to the disclosure and chemical structures of their metabolites which may be measured in bodily waste according to the disclosure.

FIG. 4 is a table showing three artificial sweeteners which are either metabolized in the body or may be chemically derivatized to a reaction product which may be more readily detected using known analytical methods. While the artificial sweetener may be the drug tag according to the disclosure, the reaction product may be the molecule that is detected during analysis of the bodily waste sample.

Figure 5:
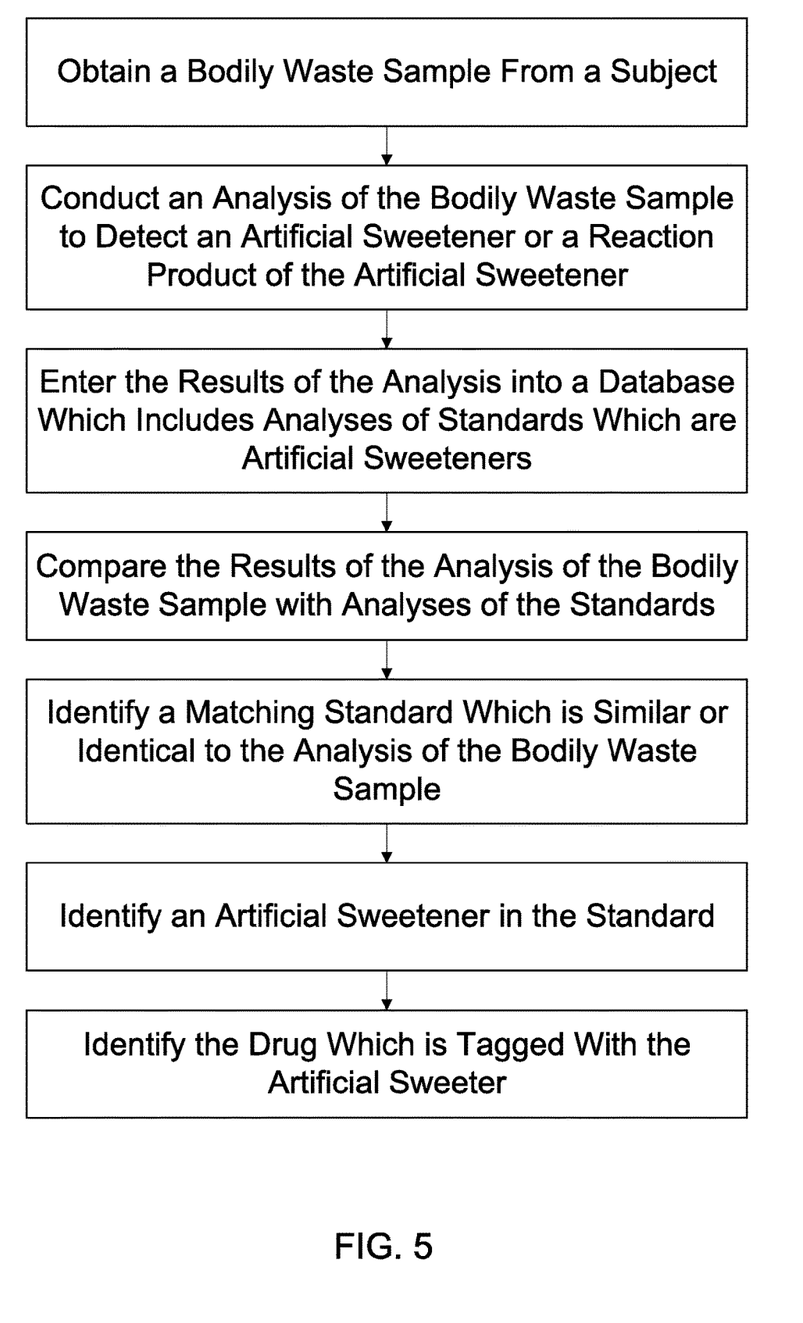
FIG. 5 provides a flow chart which includes steps which may be used in performing an embodiment of a method of using the disclosed drug tracking system to identify a drug consumed by a subject.

FIG. 5 is a flow chart which illustrates a series of steps which may be performed according to an embodiment of the disclosed drug tracking system. In the embodiment of FIG. 5, a user obtains a bodily waste sample from a subject. The subject has consumed a drug which has been tagged with an artificial sweetener according to the disclosure. The user then conducts an analysis of the bodily waste sample to detect the artificial sweetener or its reaction product using known analytical techniques. When detecting reaction products, the reaction products may be metabolites of the artificial sweetener or derivatives of the artificial sweetener which were created in vitro after collecting the bodily waste sample. The user then enters the results of the analysis into a database. The database includes standards which are analytical results that were obtained by detecting known artificial sweeteners which were used as drug tags. The user or computer readable medium associated with the database compares the results from the analysis of the subject's bodily waste with the standards stored in the database. The user or the computer readable medium identifies a matching standard. More specifically, the user or computer readable medium identifies an analytical result obtained by analyzing an artificial sweetener that is identical or similar to the analytical result obtained by analyzing the subject's bodily waste. The artificial sweetener used to create the matching standard is determined and then the drug associated with that artificial sweetener, meaning the drug that was tagged with the artificial sweetener used to create the standard, is identified. The drug the subject consumed has thereby been identified.

Figure 6:
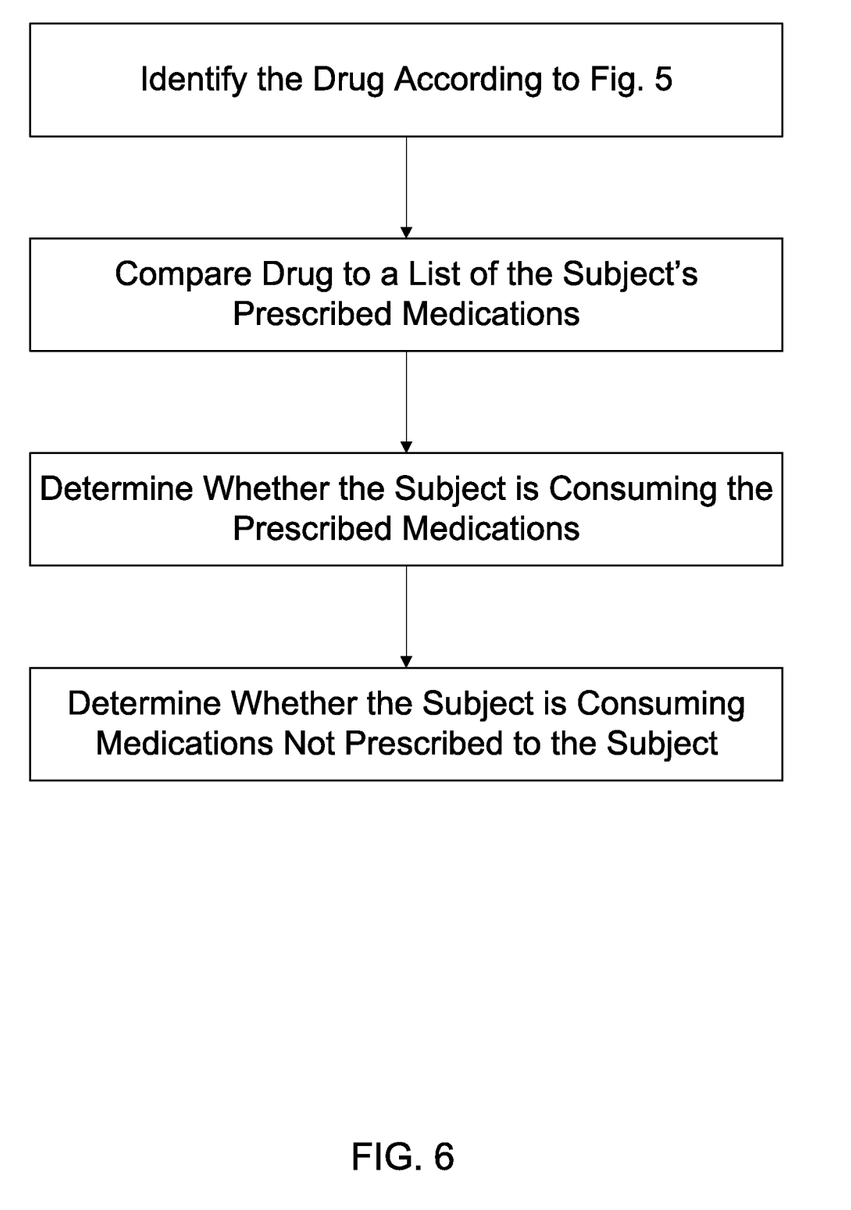
FIG. 6 provides a flow chart which includes steps in using the disclosed drug tracking system to determine if a subject is consuming medications prescribed to the subject and no others.

FIG. 6 is a flow chart which illustrates a series of steps which may be performed according to an embodiment of the disclosed drug tracking system. This method uses the disclosed drug tracking system to determine whether the subject has been consuming the drug that was prescribed to the subject. First, the identity of the drug the user has consumed is determined according to the procedure outlined in FIG. 5. In this embodiment, the database includes or has access to files that contain the drug that has been prescribed to the subject. The computer readable medium compares the drug identified as being consumed by the subject with the one or more drugs listed in the file that contains the subject's prescriptions. The computer readable medium thereby determines whether the subject has consumed the drugs which have been prescribed to the subject as well as whether the subject has consumed tagged drugs which are not prescribed to the subject.

Figure 7:
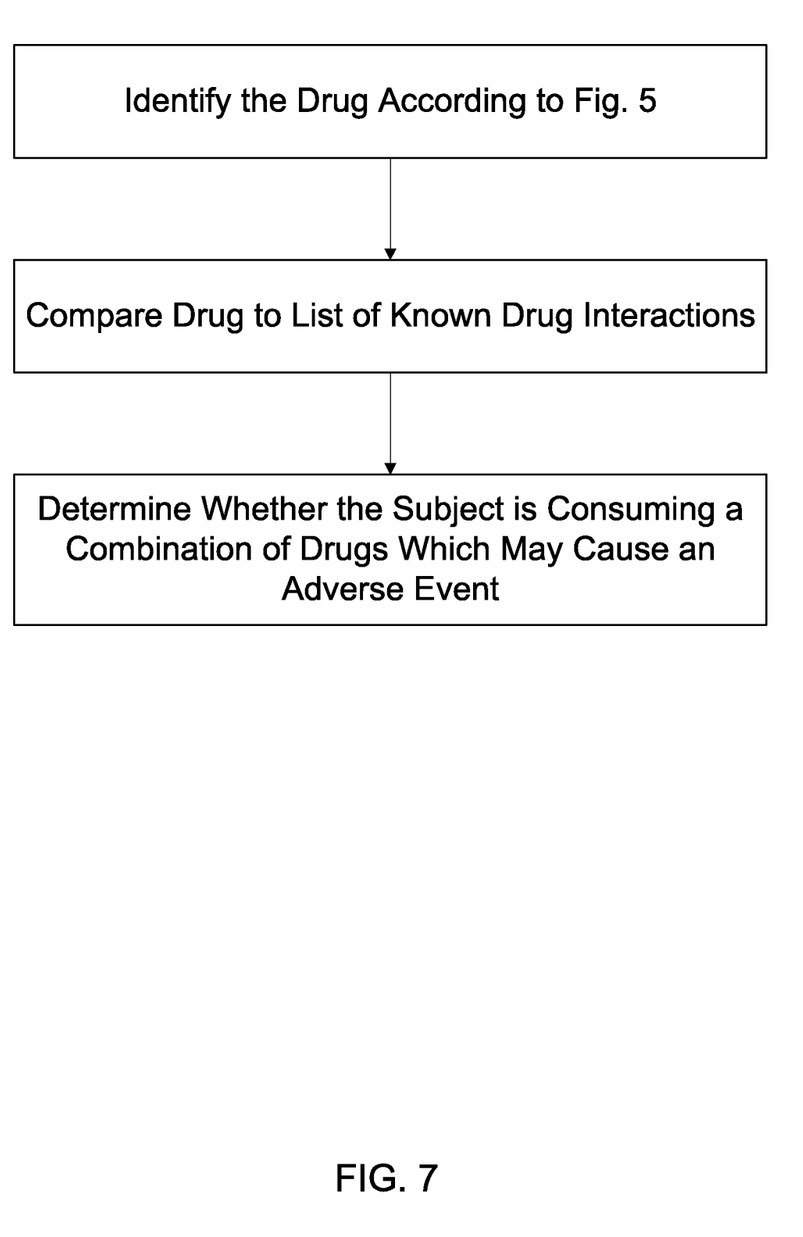
FIG. 7 provides a flow chart which includes steps in using the disclosed drug tracking system to determine if a subject is consuming medications which may lead to an adverse drug interaction.

FIG. 7 is a flow chart which illustrates a series of steps which may be performed according to an embodiment of the disclosed drug tracking system. This method uses the disclosed drug tracking system to determine whether the subject has consumed drugs which may cause an adverse drug interaction. First, the identity of the drug the user has consumed is determined according to the procedure outlined in FIG. 5. In this embodiment, the database includes or has access to files that contain known drug interactions. The drugs which the drug tracking system has identified as having been consumed by the subject are compared to the known drug interactions. The computer readable medium thereby determines whether the subject has consumed the drugs which may result in an adverse event.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of tracking drug consumption comprising the steps of:
  a. obtaining a bodily waste sample from a subject, wherein the subject has consumed a drug composition, wherein the drug composition comprises a drug tag, and wherein the drug tag comprises at least one artificial sweetener;
  b. creating an analysis of the bodily waste sample using techniques which determine the identity, quantity, or both the identity and quantity of the at least one artificial sweetener, an at least one reaction product of the at least one artificial sweetener, or a combination thereof.

2. The method of claim 1, wherein the at least one artificial sweetener is independently selected from one or more the group consisting of the following: acesulfame K, saccharine, sucralose, steviol glycoside, neotame, aspartame, cyclamic acid, calcium cyclamate, sodium cyclamate, polyethylene glycol, and sugar alcohols.

3. The method of claim 2, wherein the sugar alcohols consist of one or more of the following sugar alcohols: arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol, and xylitol.

4. The method of claim 1, wherein the reaction product of the at least one artificial sweetener is selected from the group consisting of the following: cyclohexylamine, steviol glucuronide, and N—[N-(3,3-dimethylbutyl)-L-alpha-aspartyl]-L-phenylalanine.

5. The method of claim 1, further comprising the step of reacting the bodily waste sample to derivative the at least one artificial sweetener present in the bodily waste sample.

6. The method of claim 1, wherein the analysis of the bodily waste sample comprises one or more of the following analytical techniques: gas chromatography-mass spectrometry, liquid chromatography, capillary zone electrophoresis with UV absorbance, high performance liquid chromatography with UV absorbance, reverse-phase chromatography, fluorescence spectroscopy, high performance thin layer chromatography, infrared spectroscopy, UV spectroscopy, near IR spectroscopy, nuclear magnetic resonance, ion mobility spectrometry, liquid chromatography-ion mobility spectroscopy, liquid chromatography-electrochemical detection, liquid chromatography-UV spectroscopy with a normal UV photodetector, thin layer chromatography, liquid chromatography, and Raman spectroscopy.

7. The method of claim 1, wherein the drug tag comprises a plurality of artificial sweeteners in a defined ratio.

8. The method of claim 1, wherein steps (a) and (b) are performed a plurality of times, and further comprising the step of performing a trending analysis.

9. The method of claim 1, wherein para-aminobenzoic acid is added to the drug composition as a biomarker, and further comprising the steps of:
  a. determining the quantity of para-aminobenzoic acid in the bodily waste sample; and
  b. expressing the quantity of the at least one artificial sweetener, the at least one reaction product of the at least one artificial sweetener, or a combination thereof in relation to the quantity of para-aminobenzoic acid.

10. A method of tracking drug consumption comprising the steps of:
  a. obtaining a bodily waste sample from a subject, wherein the subject has consumed at least one drug composition, wherein each of the at least one drug composition comprises at least one of a plurality of unique drug tags, and wherein at least one of the plurality of unique drug tags comprises at least one artificial sweetener;
  b. creating an analysis of the bodily waste sample using techniques which determine an identity, a quantity, or both the identity and the quantity of the at least one artificial sweetener, an at least one reaction product of the at least one artificial sweetener, or a combination thereof;
  c. comparing the analysis of the bodily waste sample to at least one standard, wherein each of the at least one standard comprises an analysis of the at least one of the plurality of unique drug tags comprising at least one artificial sweetener or a reaction product of the at least one artificial sweetener; wherein each standard comprises an analysis of a different one of the plurality of unique drug tags comprising at least one artificial sweetener or the reaction product of the at least one artificial sweetener;
d. identifying at least one matching standard, wherein each of the at least one matching standard comprises a standard which at least partially matches the analysis of the bodily waste sample;
e. identifying the at least one artificial sweetener used to create each of the at least one matching standard;
f. identifying the at least one of the plurality of unique drug tags which comprises the at least one artificial sweetener used to create the at least one matching standard;
g. identifying the at least one drug composition which comprises the at least one of the plurality of unique drug tags identified in step "f".

11. The method of claim 10, wherein the at least one standard is stored in a database, and wherein a computer readable medium performs steps "c" through "g" of claim 10.

12. The method of claim 10, wherein the at least one artificial sweetener is independently selected from one or more the group consisting of the following: acesulfame K, saccharine, sucralose, steviol glycoside, neotame, aspartame, cyclamic acid, calcium cyclamate, sodium cyclamate, polyethylene glycol, and sugar alcohols.

13. The method of claim 12, wherein the sugar alcohols consist of one or more of the following sugar alcohols: arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol, and xylitol.

14. The method of claim 10, wherein the reaction product of the at least one artificial sweetener is selected from the group consisting of the following: cyclohexylamine, steviol glucuronide, and N—[N-(3,3-dimethylbutyl)-L-alpha-aspartyl]-L-phenylalanine.

15. The method of claim 10, further comprising the step of reacting the bodily waste sample to derivative the at least one artificial sweetener present in the bodily waste sample.

16. The method of claim 10, wherein the analysis of the bodily waste sample comprises one or more of the following analytical techniques: gas chromatography-mass spectrometry, liquid chromatography, capillary zone electrophoresis with UV absorbance, high performance liquid chromatography with UV absorbance, reverse-phase chromatography, fluorescence spectroscopy; high performance thin layer chromatography, infrared spectroscopy, UV spectroscopy, near IR spectroscopy, nuclear magnetic resonance, ion mobility spectrometry, liquid chromatography-ion mobility spectroscopy, liquid chromatography-electrochemical detection, liquid chromatography-UV spectroscopy with a normal UV photodetector, thin layer chromatography, liquid chromatography, and Raman spectroscopy.

17. The method of claim 10, wherein the at least one drug composition comprises a plurality of artificial sweeteners in a defined ratio.

18. The method of claim 10, wherein steps (a) through (g) are performed a plurality of times, and further comprising the step of performing a trending analysis.

19. The method of claim 10, wherein para-aminobenzoic acid is added as a biomarker to the at least one drug composition, and further comprising the steps of:
a. determining the quantity of para-aminobenzoic acid in the bodily waste sample; and
b. expressing the quantity of the at least one artificial sweetener, the at least one reaction product of the at least one artificial sweetener, or a combination thereof in relation to the quantity of para-aminobenzoic acid.

20. The method of claim 10, further comprising the step of comparing the at least one unique drug composition with a list of medications that are prescribed to the subject.

* * * * *